(12) United States Patent
Polansky (10) Patent No.: US 12,312,602 B2
(45) Date of Patent: May 27, 2025

(54) APPARATUS AND METHOD FOR HARVESTING AND PREPARING VIABLE STEM CELLS

(71) Applicant: Glenn Polansky, Ridgewood, NJ (US)

(72) Inventor: Glenn Polansky, Ridgewood, NJ (US)

( * ) Notice: Subject to any disclaimer, the term of this patent is extended or adjusted under 35 U.S.C. 154(b) by 665 days.

(21) Appl. No.: 17/142,355

(22) Filed: Jan. 6, 2021

(65) Prior Publication Data

US 2021/0147806 A1   May 20, 2021

Related U.S. Application Data

(63) Continuation of application No. 15/880,730, filed on Jan. 26, 2018, now Pat. No. 10,913,931.

(60) Provisional application No. 62/452,960, filed on Jan. 31, 2017.

(51) Int. Cl.
| | |
|---|---|
| *C12N 5/0775* | (2010.01) |
| *A01N 1/02* | (2006.01) |
| *A61K 35/35* | (2015.01) |
| *B01J 19/10* | (2006.01) |
| *C12M 1/34* | (2006.01) |
| *C12M 1/42* | (2006.01) |
| *C12M 3/06* | (2006.01) |

(Continued)

(52) U.S. Cl.
CPC ............. *C12N 5/0667* (2013.01); *A01N 1/02* (2013.01); *A61K 35/35* (2013.01); *B01J 19/10* (2013.01); *C12M 1/42* (2013.01); *C12M 3/06* (2013.01); *C12M 41/12* (2013.01); *C12N 5/0081* (2013.01); *C12N 13/00* (2013.01)

(58) Field of Classification Search
None
See application file for complete search history.

(56) References Cited

U.S. PATENT DOCUMENTS

| | | | | |
|---|---|---|---|---|
| 1,236,929 A | * | 8/1917 | Hauck | A47G 29/18 211/74 |
| 4,874,137 A | * | 10/1989 | Chiba | C12N 1/066 241/1 |

(Continued)

FOREIGN PATENT DOCUMENTS

| | | |
|---|---|---|
| AU | 2011352928 A1 | 7/2013 |
| EP | 2792741 A1 | 10/2014 |

OTHER PUBLICATIONS

Qsonica ("431C2"). Video at about 25-30 seconds in. From YouTube, Jun. 9, 2016: http://www.youtube.com/watch?v=j-JGBoOxfPQ. Accessed May 26, 2023. (Year: 2016).*

(Continued)

*Primary Examiner* — Holly Kipouros
*Assistant Examiner* — Nathan G Esperon
(74) *Attorney, Agent, or Firm* — Werschulz Patent Law, LLC; Patricia P. Werschulz, Esq.

(57) ABSTRACT

A method of preparing viable stromal and mesenchymal stem cells from adipose tissue that produces high quality and high counts of stem cells with a low risk of contamination. The apparatus provides ultrasonic waves through a constant temperature bath to the tissue held in a sterile sonication container such as a test tube or jar. No sonication probe touches the tissue or the cells during the process. The stem cells produced are ready to be administered to a patient.

2 Claims, 8 Drawing Sheets

(51) Int. Cl.
*C12N 5/00* (2006.01)
*C12N 13/00* (2006.01)

(56) References Cited

U.S. PATENT DOCUMENTS

| | | | | |
|---|---|---|---|---|
| 4,930,532 | A * | 6/1990 | Mayer | A61C 19/002 |
| | | | | 366/127 |
| 8,440,440 | B2 | 5/2013 | Victor | |
| 10,473,568 | B2 * | 11/2019 | Panteleeva | C12Q 1/6806 |
| 2006/0051865 | A1 | 3/2006 | Higgins et al. | |
| 2009/0079300 | A1 * | 3/2009 | Hielscher | B01J 19/008 |
| | | | | 310/324 |
| 2011/0233148 | A1 * | 9/2011 | Antonchuk | B01D 35/30 |
| | | | | 210/477 |
| 2013/0189234 | A1 | 7/2013 | Victor | |
| 2014/0255356 | A1 * | 9/2014 | Victor | A61N 7/00 |
| | | | | 435/378 |
| 2016/0107158 | A1 * | 4/2016 | Gray | B01L 3/5082 |
| | | | | 73/864.91 |

OTHER PUBLICATIONS

Qsonica ("Cup Horn"). From WebArchive, Sep. 16, 2015: https://web.archive.org/web/20150916032608/sonicator.com/33-cup-horn-55-cup.html. Accessed May 26, 2023. (Year: 2016).*

Qsonica. "Dissolution in 15ml tube". YouTube video URL: youtube.com/watch?v=ShMNMuWUTzE&t=3s. Posted Jul. 18, 2016. (Year: 2016).*

Qsonica. "Sonicator". Manual URL: https://web.archive.org/web/20131228000502/http://www.sonicator.com/literature/manuals/Catalog.pdf. Recorded on Dec. 28, 2013. (Year: 2013).*

Qsonica ("431C2"). Additional images from previous prior art video. From YouTube, Jun. 9, 2016: http://www.youtube.com/watch?v=j-JGBoOxfPQ. 2016. (Year: 2016).*

Amirkhani et al, "A rapid sonication based method of preparation of stromal vascular fraction and mesenchymal stem cells from fat tissue" Bioimpato, 2016:6(2): 99-104 TUOMS Publishing Group, Tabriz, Iran.

Araujo et al. "A journey through Proteosonics." Talanta 121 (2014): 71-80 (Year: 2014).

Nemecek et al. "Red-backed vole brain promotes highly efficient in vitro amplification of abnormal prion protein from macaque and human brains infected with variant Creutzfeldt-Jakob disease agent." PloS One 8.10 (2013) (Year: 2013).

QSonica Sonicatiors "Ultrasonic Liquid Processors Catalog", available at the company webpage https://www.sonicator.com/, accessed May 7, 2020, copyright 2018 (Year: 2018).

Santos et al. "Trends in ultrasonic-based equipment for analytical sample treatment." Talanta 73.5 (2007): 795-802 (Year: 2007).

* cited by examiner

APPARATUS AND METHOD FOR HARVESTING AND PREPARING VIABLE STEM CELLS

CROSS-REFERENCE TO RELATED APPLICATIONS

This application is a continuation of the nonprovisional utility application of the non-provisional utility patent application, Ser. No. 15/880,730, filed in the United States Patent Office on Jan. 26, 2018 claiming priority to the provisional utility patent application, Ser. No. 62/452,960, filed in the United States Patent Office on Jan. 31, 2017 and claims the priority thereof and is expressly incorporated herein by reference in its entirety.

TECHNICAL FIELD

The present disclosure relates generally to an apparatus and a method of harvesting and preparing stem cells. More particularly, the present disclosure relates to a method of harvesting stem cells and an apparatus for extracting said stem cells from adipose tissue for administration to a patient.

BACKGROUND

The use of stem cells to treat a large catalog of diseases and disease states continues to grow as more and more research is performed. Many patients receive autologous stem cells, that is stem cells harvested from their own bodies.

Stem cells are undifferentiated biological cells that can differentiate into specialized tissues forming skin, bones and organs. Originally when stem cells were first identified, their existence was thought to be only in embryonic cells since the embryo starts with identical cells from the fertilized egg that eventually differentiate into specific specialized cells, transforming the embryo into a fetus.

Scientists did not know that stem cells existed in adult bodies until they were discovered in bone marrow, blood and even fatty deposits in the body. These cells are harvested and injected into the donor to repair damaged tissue.

In autologous administration, because the patient receives their own cells back, the procedure is relatively safe.

Many practitioners extract the stem cells from adipose tissue from liposuction of fatty deposits and enzymatically lyse the adipose tissue to release the stem cells from the tissues. Others use various mechanical means of breaking up the fatty tissue to release the stem cells.

A common technique involves a sonication probe immersed into the actual sample of adipose tissue that increases the possibility of cross-contamination with pathogens as well as other cells from other donors. This can cause a hemolytic reaction with varying consequences, ranging from an allergic type reaction to life-threatening.

Another technique is to use enzymes to lyse the cells in the adipose tissue. this technique has very load yields in addition to contaminating the stem cells with enzymes from animal sources that could cause an allergic type of reaction.

While these methods may be suitable for the particular purpose employed, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed, and it is contemplated that the claims may encompass one or more of the conventional technical aspects discussed herein.

BRIEF SUMMARY

An aspect of an example embodiment in the present disclosure is to provide a method of preparing stem cells with minimal risk of contamination. Accordingly, an aspect of an example embodiment in the present disclosure provides a method and apparatus that lyses tissues through an ultrasonication apparatus that does not touch or contaminate the tissues containing stem cells.

Another aspect of an example embodiment in the present disclosure is to provide a method of preparing stem cells that produces high quality and high counts of viable stem cells. Accordingly, the present disclosure provides a method that sonicates tissues at a constant temperature.

The present disclosure describes a method of preparing viable stem cells from adipose tissue that produces high quality and high counts of stem cells with a low risk of contamination. The apparatus provides ultrasonic waves through a constant temperature bath to the tissue held in a sterile sonication container such as a test tube or jar. No sonication probe touches the tissue or the cells during the process. The stem cells produced are ready to be administered to a patient.

The present disclosure defines a standard procedure for the isolation of stromal vascular fraction (SVF) from lipoaspirate using a closed-system sonication-driven process that uses mechanical shaking by sonication of the tissue to separate the SVF followed by its concentration by centrifugation.

The present disclosure provides holders for containers of adipose tissue lipoaspirate that suspends the containers above the sonication cup horn, helping to maintain a constant temperature of the adipose tissue in conjunction with a constant temperature water bath The present disclosure addresses at least one of the foregoing disadvantages explained hereinabove such as low yield and risk of contamination. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

The scope of this disclosure is to define the core steps in the isolation, harvesting and concentration of SVF (stromal vascular fraction) cells from lipoaspirate collected from human subjects. The processes are designed to be conducted inside a controlled access clean room (at least ISO 8, Class 100,000) and all the sterile processes are conducted inside an isolator biosafety cabinet (ISO 5, Class 100 air quality.)

Figure 1:
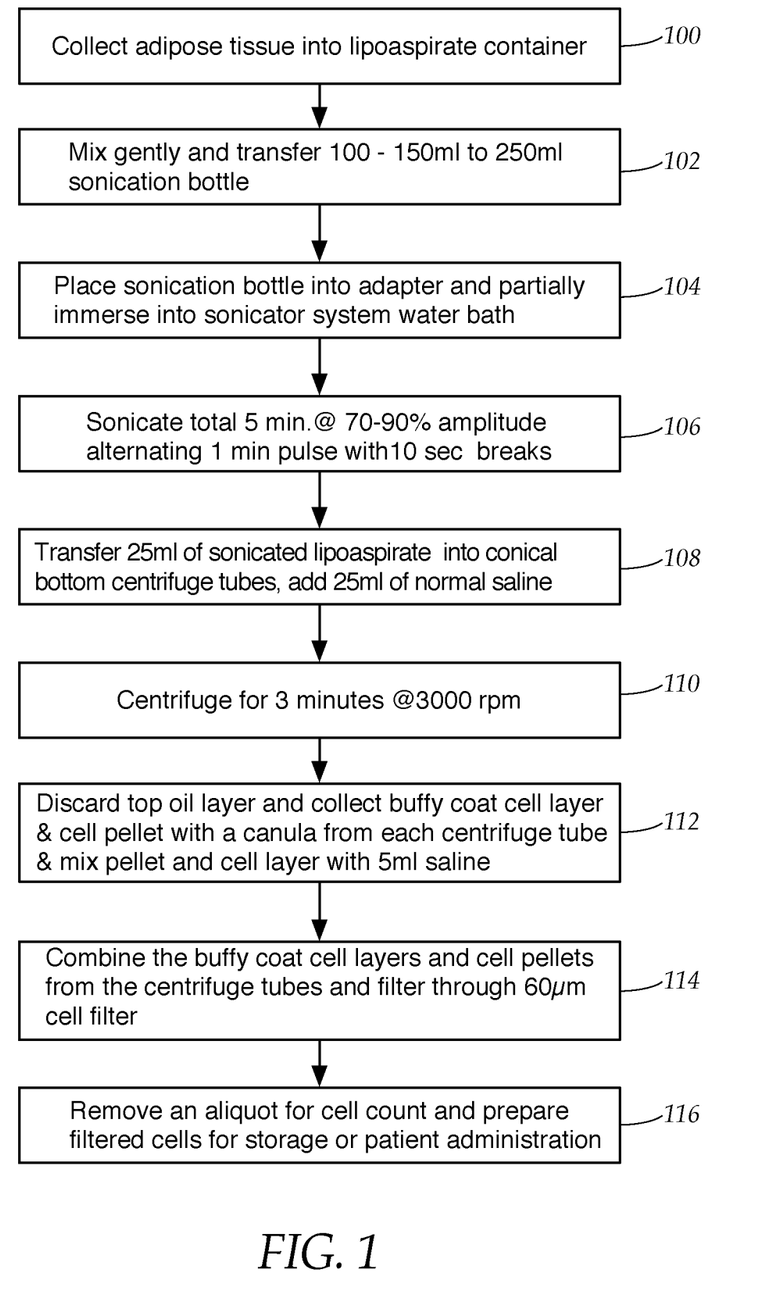
FIG. 1 is an example embodiment of a flow chart for the process of harvesting stem cells from adipose tissue using a sonication bottle.

FIG. 1 illustrates a process for harvesting stem cells from adipose tissues. In many cases the tissue is collected through liposuction or similar surgical techniques. However, the technique of collecting the tissue is not a limitation. While this procedure is used primarily for autologous administration, donor stem cells for heterologous administration is possible using the same techniques as described below. Similarly, if the source of the SVF cells are other bodily tissues that is obtained through techniques other than liposuction, this is not a limitation of the method.

It is understood to those of ordinary skill the art that certain standard practices are part of this procedure. All steps described are performed using sterile techniques for transfer of biological materials. All transfers are performed inside an isolator hood, using sterile containers and sterile transfer devices under sterile conditions. All volumes are approximate.

All procedures are performed under current Good Laboratory Practices as defined in 21 CFR Part 1271, 21 CFR Part 11, Public Health Services Act, Section 361, FDA Guidance on GTP and GMP for cellular based products and CLIA (Clinical Laboratory Improvement Amendments of 1988) regulations as well as all local, state and federal regulations for the handling of biological materials for administration to humans. Additionally, standard laboratory techniques and equipment operations are used unless otherwise described and noted.

The term "saline" is defined as normal saline, also referred to as physiological saline or isotonic saline, is an aqueous solution of 0.90% w/v of NaCl (sodium chloride).

Referring to FIG. 1, the process using a sonication bottle is disclosed. The sonication bottle is capable of holding at least 150 ml of material. The adipose tissue is collected into a lipoaspirate container 100. As explained hereinabove, other tissue sources may be used and the term lipoaspirate container refers to any sterile container suitable for maintaining tissue samples under sterile conditions.

The tissue is mixed and transferred to a 250 ml sonication bottle, transferring preferably 100 ml to 150 ml quantities 102. If larger quantities are required for treatment, a larger container is used; conversely, if small quantities are required, a sterile conical bottom tube is used as explained hereinbelow.

The sonication bottle is placed into a bottle adapter and partially immersed into the sonicator system water bath above a cup horn of the sonicator 104. The sample is sonicated 5 minutes in total @ 70-90% amplitude alternating 1-minute pulse with interjecting 10 second to 1-minute rests, preferably a minimum of 10 seconds 106. The sonicator operates at 20 kHz. The sample is kept at a constant temperature 20° C. by circulating water maintained at a constant temperature.

Sonication produces heat and the constant temperature bath dissipates the heat, keeping the sample at low room temperature, thereby increasing the vitality of the stem cells in the process, and avoiding heat denaturing. Maintaining the sonication bottle above and not on the cup horn also decreases the transfer of heat No probe is used to lyse the cells through sonication. Nothing enters the sonication bottle except the sample itself which is closed during the sonication process. This minimizes the risk contamination from pathogens or cross-contamination with another patient's cells.

After sonication, aliquots of approximately 25 ml of sonicated lipoaspirate is transferred to conical bottom centrifuge tubes and 25 ml of saline is added 108. The aliquots are centrifuged at 3000 rpm (revolutions per minute), lasting for a minimum of 3 minutes 110.

The supernatant oil layer is discarded after centrifuging and the buffy coat cell layer and cell pellet are collected through a cannula 112. The buffy coats and cell pellets from the centrifuge tubes are mixed together and a small amount of saline, approximately 5 ml, is added 114. The mixture is filtered through a sterile 60 μm cell filter 114. An aliquot for cell count is removed and the stem cells are ready for administration or storage, pending release from quarantine 116.

Figure 2:
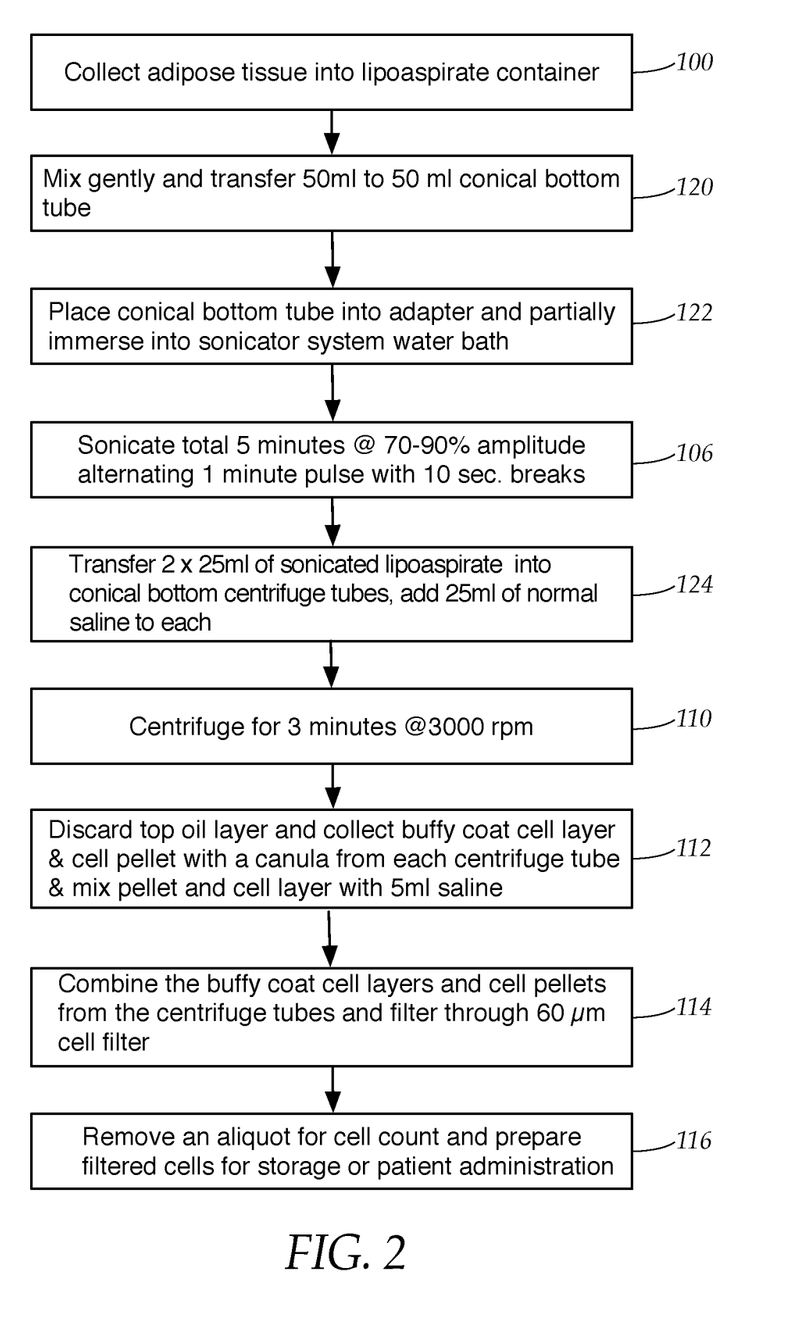
FIG. 2 is an example embodiment of a flow chart for the process of harvesting stem cells from adipose tissue using a sonication bottle.

FIG. 2 shows the process using a conical bottom tube. Similar to the process in FIG. 1, except small volumes are transferred into fewer containers.

The adipose tissue is collected into a lipoaspirate container 100.

The tissue is mixed and 50 ml is transferred to a 50 ml sterile conical bottom tube 120. If larger quantities are required for treatment, a larger container is used as explained hereinabove.

The sterile conical bottom tube is placed into a tube adapter and partially immersed into the sonicator system water bath above a cup horn of the sonicator 122. The sample is sonicated 5 minutes in total @ 70-90% amplitude alternating 1-minute pulse with 10 second to 1-minute rests, preferably a minimum of 10 seconds 106. The sonicator operates at 20 kHz. The sample is kept at a constant temperature 20° C. by circulating water maintained at a constant temperature.

After sonication, aliquots of approximately 25 ml of sonicated lipoaspirate is transferred to two conical bottom centrifuge tubes and 25 ml of saline is added to each 124.

The aliquots are centrifuged at 3000 rpm, the centrifuging lasting for a minimum of 3 minutes 110.

The supernatant oil layer is discarded after centrifuging and the buffy coat cell layer and cell pellet are collected through a cannula 112. The buffy coats and cell pellets from the centrifuge tubes are mixed together and a small amount of saline, approximately 5 ml, is added 114. The mixture is filtered through a sterile 60 μm cell filter 114. An aliquot for cell count is removed and the stem cells are ready for administration or storage, pending release from quarantine 116.

As one can see, there are no significant changes between the two procedures except the size of the containers. The operating parameters remain the same.

The process begins with placing a container containing adipose tissue above the cup horn located in in a water bath of a sonicator system. The water bath maintains the container and its contents at a constant temperature, preferably at or around 20° Celsius. The container and its contents are sonicated with pulsing for a total of five minutes, with at least 10 second rests after each one-minute interval. The adipose tissue resulting from sonication is mixed with equal volumes of saline, centrifuged at 3000 rpm for 3 minutes, discarding the oily supernatant, adding a small amount of saline and filtering with a 60 μm filter The sonicating step is performed at 70% to 90% amplitude of the sonicator system operating at 20 kHz.

In both examples, the container, regardless if it is a bottle or conical tube containing adipose tissue is suspended a minimum of 3 mm above by placing the container in an adapter. The container is not in contact with the cup horn located in in the water bath of the sonicator system.

Regardless of the container, the sonicator system lacks a sonicating probe in contact with the adipose tissue.

Figure 3:
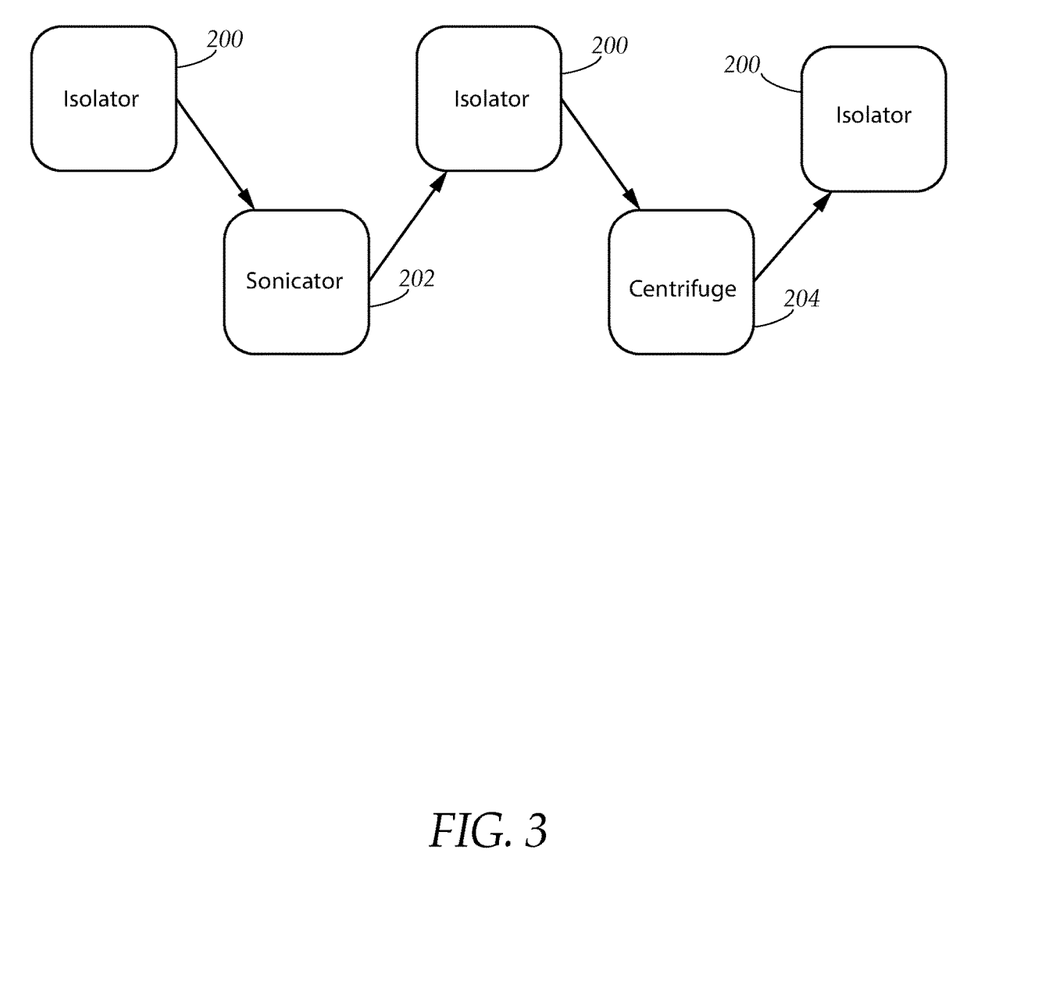
FIG. 3 is a block diagram of a plurality of equipment for harvesting stem cells from adipose tissue.

FIG. 3 shows the material flow. The material is transferred into the sonication bottle or conical bottom tube from the lipoaspirate container in the isolator hood 200 at the top. The sonication bottle or tube is transferred to the sonication system in the lower drawing 202. After sonication, the container or tube is returned to the isolator hood 200 for mixing with saline and transferred to centrifuge tubes. The centrifuge tubes are closed, removed from the isolator hood and placed in the centrifuge 204. After centrifuging, the tubes are returned to the isolator hood for transfer, filtering, sampling and final transfer prior to administration 202.

As one of ordinary skill in the art can appreciate, the material flow may be between one or more isolators and this is not a limitation. In some laboratories, each operation may have a separate isolator for each activity or all activities requiring isolation may occur in the same isolator.

Figure 4:
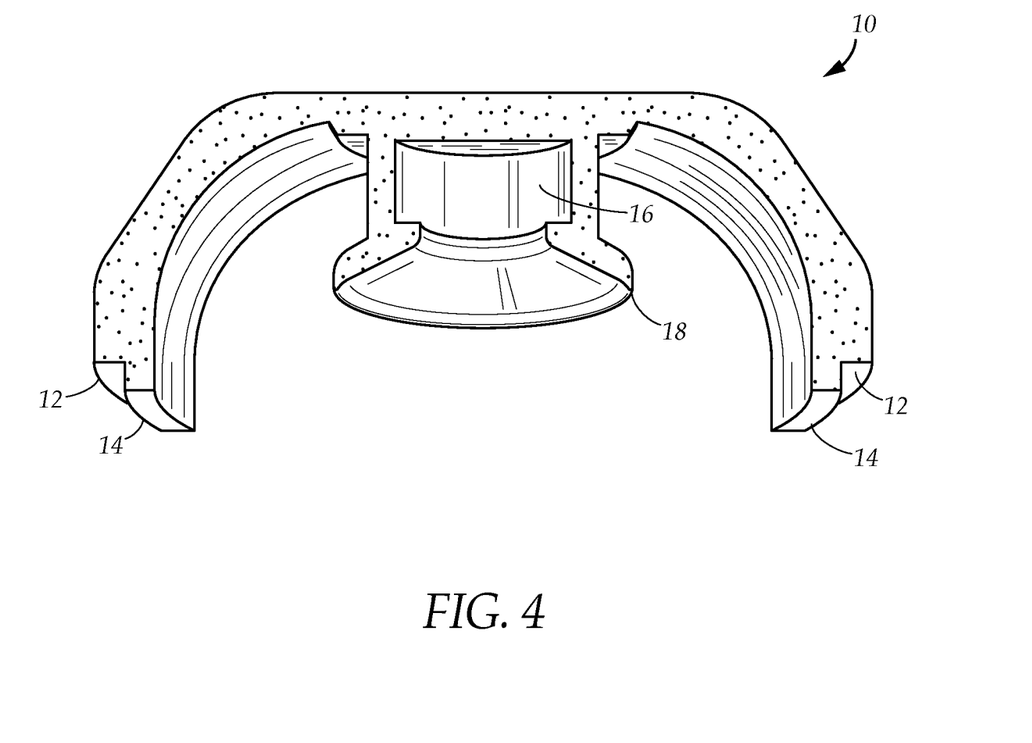
FIG. 4 is an example embodiment of a sonication bottle adapter.
Figure 5:
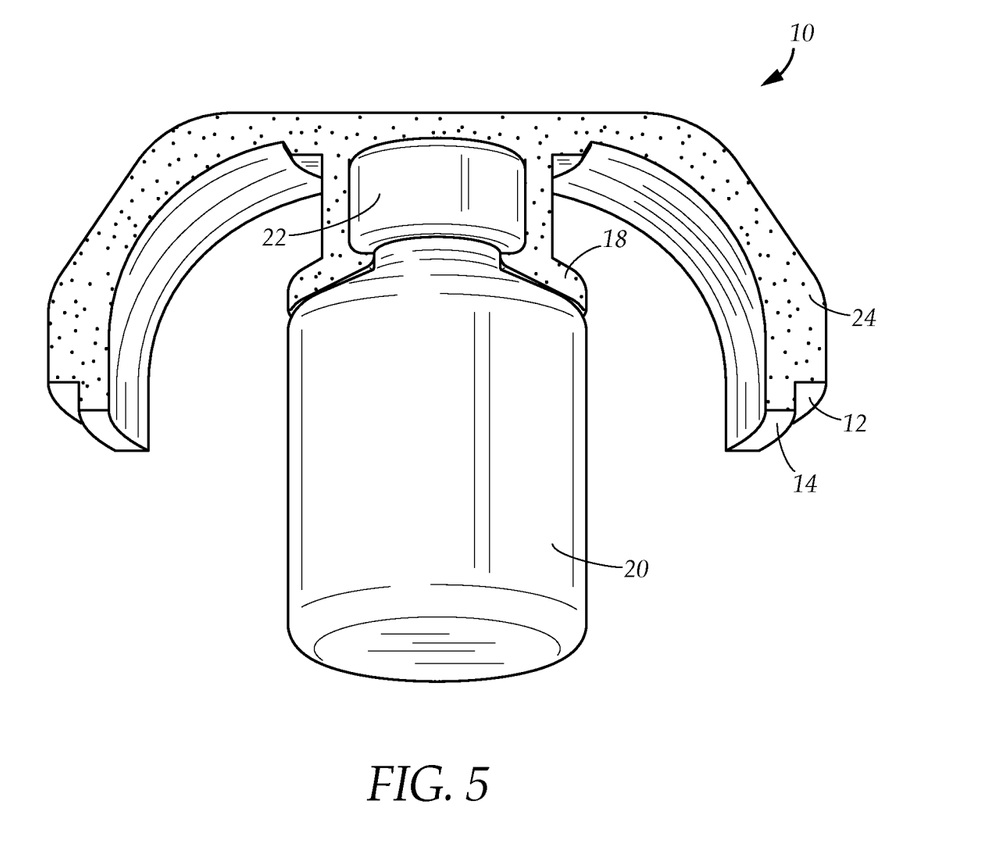
FIG. 5 is an example embodiment of a sonication bottle adapter and sonication bottle.

FIGS. 4 and 5 show an adapter 10 for holding the sonication bottle 20. This adapter 10 allows the use of larger containers than previously known in the art which increases the through-put of the process, allowing a patient's entire sample to be processed at once.

The adapter 10 has a pair of wings 24 extending out from a recess 16 for a cap 22 of the sonication bottle 20. The recess 16 is formed by a pair of arms 18 to conform to the shape of cap 22 and shoulder of the sonication bottle 20. The wings 24 with a lip 14 and a groove 12. The adapter 10 may be preferably disposable or made from material that withstands repeated sterilization without losing strength and shape.

Figure 6:
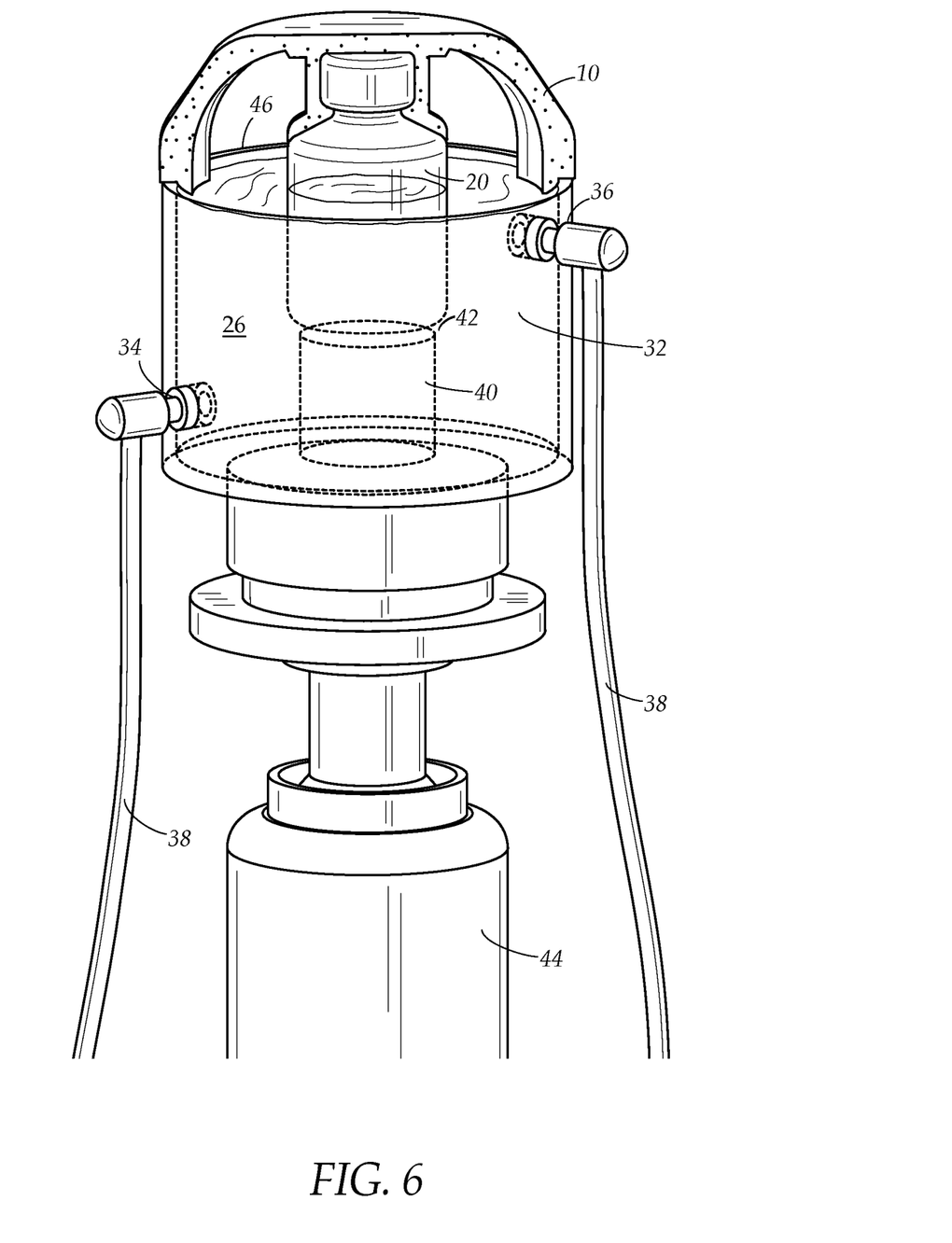
FIG. 6 is an example embodiment of the sonication bottle in place in the water bath of the sonication system.

As shown in FIG. 6, the groove 12 sits on the rim 46 of the water bath and lip 14 of the adapter presses against the inside wall of the water bath 32.

FIG. 6 shows the sonication bottle 20 suspended above the ultrasonic cup horn 40 of the sonicator system, where the ultrasonic waves are augmented. There is a gap 42 of at least 3 mm between the sonication bottle 20 and the cup horn 40, with no direct contact. This allows the ultrasonic waves to be transmitted through the water rather than through the glass walls of the sonication bottle 20, reducing the possibility of shattering the glass.

The circulating tubing 38 of the water system is shown with an inlet 34 and an outlet 36 the water 26 mainly covering the lower portion of the sonication bottle where a sample is normally contained. The water bath 32 with the sonication bottle 20 containing lipoaspirate suspended above the cup horn 40 sits on top of a sonic wave generator 44 of sonication system.

Figure 7:
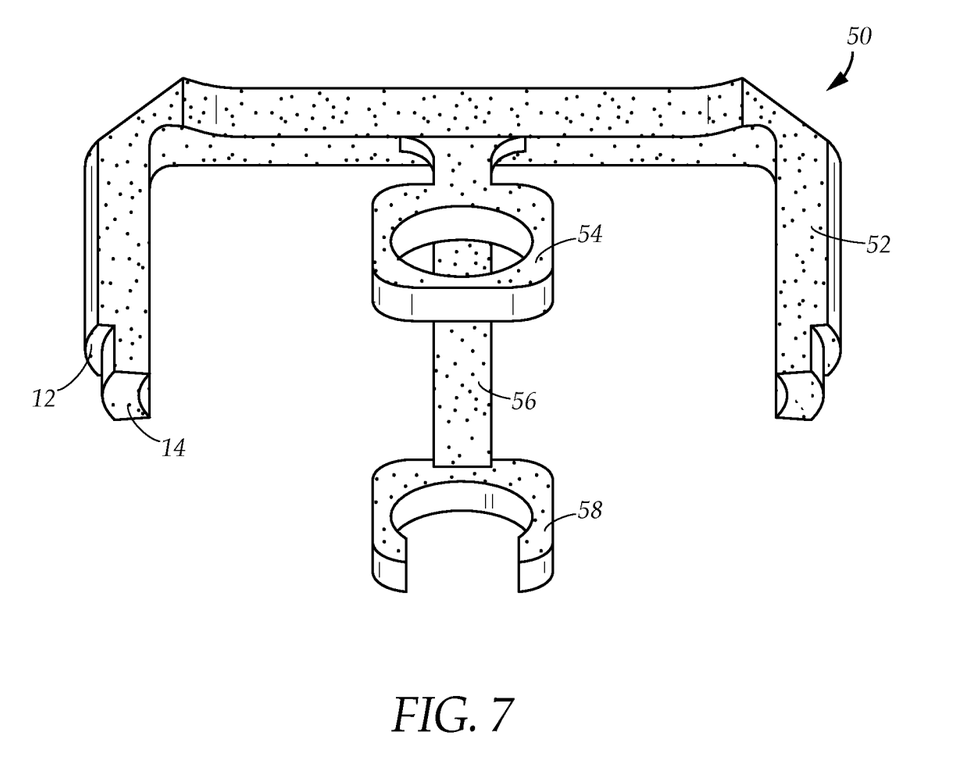
FIG. 7 is an example embodiment of a conical bottom tube holder.
Figure 8:
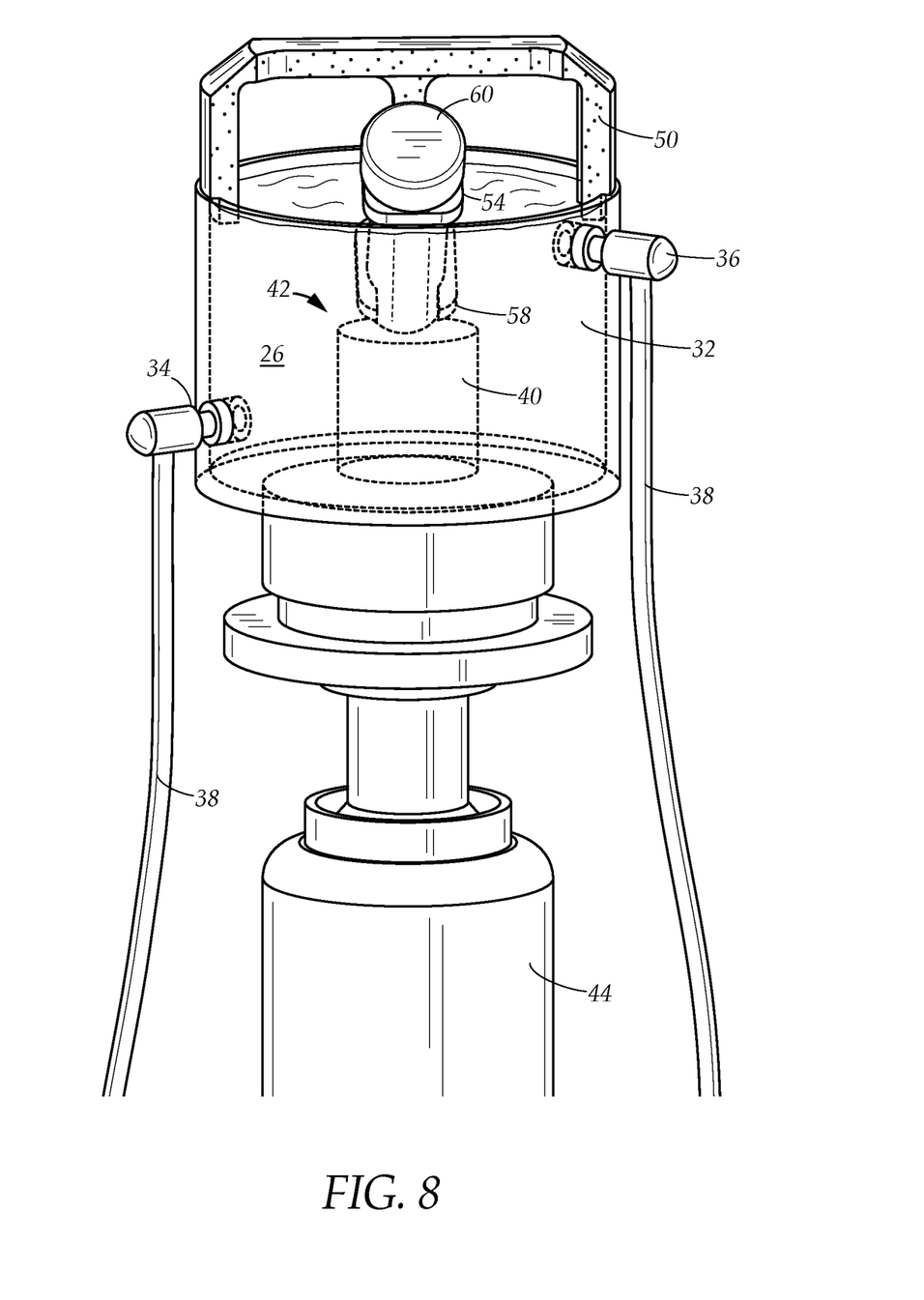
FIG. 8 is an example embodiment of the conical bottom tube in place in the water bath of the sonication system.

FIGS. 7 and 8 shows a conical bottom tube adapter 50 for holding the conical bottom tube 60 in the water bath 32. The adapter 50 has a pair of wings 52 extending outwardly that end in the groove 12 and the lip 14 and sit on the rim 46 of the water bath 32 as described hereinabove with reference to the sonication bottle adapter described hereinabove.

The conical bottom tube adapter 50 has an upper ring 54, a lower "U"-shaped holder 58 and a bar 56 connecting the upper ring 54 and the U-shaped holder. The bar 56 is angled so that when the conical bottom tube 60 is place into the upper ring 54, the tube is angled, maximizing the surface area of the contents therein.

FIG. 8 shows the adapter 50 holding the conical bottom tube 60 above the cup horn 40. The tube 60 is held at an angle and the lipoaspirate inside is mainly immersed in the water bath 32 to maximize the exposure to the ultrasonic waves. The tube likewise is held approximately 3 mm above the cup horn 40 creating a gap 42.

The adapter 50 may be preferably disposable or made from material that withstands repeated sterilization without losing strength and shape.

The example embodiment of the method as described hereinabove results in high cell counts as shown in Table 1 providing data on ten patients. The

TABLE 1

| Patient | Total Cell Count/ml | Cell Count in 120 ml | Total % Viability |
|---|---|---|---|
| 1 | 14,200,000 | 1,704,000,000 | 98.30% |
| 2 | 15,700,000 | 1,884,000,000 | 100% |
| 3 | 24,800,000 | 2,976,000,000 | 95% |
| 4 | 14,500,000 | 1,740,000,000 | 100% |
| 5 | 14,200,000 | 1,704,000,000 | 100% |
| 6 | 11,600,000 | 1,392,000,000 | 100% |
| 7 | 10,200,000 | 1,224,000,000 | 100% |
| 8 | 19,200,000 | 2,304,000,000 | 92.9% |
| 9 | 15,600,000 | 1,872,000,000 | 83.3% |
| 10 | 12,200,000 | 1,464,000,000 | 100% |

The first column is a patient identifier. The second column is the cell count per ml. The third column shows the number of cells administered to the patient, typically in a 120 ml dose. The fourth column is the percentage of viable cells determined in the aliquot. The harvested cells include immunophenotypes CD31, CD34 and CD45, which are protein markers expressed by various types of cells, involved in tissue formation, immune response and other cellular functions. These cells also appear to co-express CD73, another protein marker, as well as appear to exhibit immunophenotypic characteristics of non-cultured MSC (mesenchymal stem cells). MSC are multipotent stromal cells that can differentiate into a variety of cell types, including osteoblasts (bone cells), chondrocytes (cartilage cells), myocytes (muscle cells) and adipocytes.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a method of harvesting viable stromal and mesenchymal stem cells and an apparatus for extracting said stem cells from fatty cells for administration to a patient. The disclosure is illustrated by example in the drawing figures, and throughout the written description. It should be understood that numerous variations are possible, while adhering to the inventive concept. Such variations are contemplated as being a part of the present disclosure.

What is claimed is:

1. An apparatus for harvesting and preparing stem cells for administration or storage, comprising:
    a conical bottom centrifuge tube;
    a sonicator system having a water bath with a rim and a cup horn in said water bath; and
    an adapter configured for suspending the conical bottom centrifuge tube in the water bath above and not in contact with the cup horn located in in the water bath of the sonicator system, said adapter having an upper ring connecting to a lower "U" shaped holder by an angled bar that maintains the conical bottom centrifuge tube at an angle when placed in the upper ring and lower "U" shaped holder, said angled bar having a top, said adapter having a pair of wings further extending parabolically from the top of the angled bar, each wing ending with a lip and a groove configured to rest on the rim of the bath.

2. An apparatus for harvesting and preparing stem cells for administration or storage, comprising:
    a sonicator system having a water bath having a rim and a cup horn in said water bath; and
    an adapter configured for suspending a container in the water bath above and not in contact with the cup horn located in the water bath of the sonicator system, said adapter having a pair of arms extending parabolically from a recess, said recess configured to the shape of a sonication bottle cap and shoulder, said adapter having a pair of wings further extending parabolically from the recess, each wing ending with a lip and a groove configured to rest on the rim of the bath.

* * * * *